(12) United States Patent
Chou et al.

(10) Patent No.: US 7,501,258 B2
(45) Date of Patent: Mar. 10, 2009

(54) PENICILLIN G BIOSENSOR, SYSTEMS COMPRISING THE SAME, AND MEASUREMENT USING THE SYSTEMS

(75) Inventors: Jung-Chuan Chou, Yunlin Hsien (TW); Chin-Hsien Yen, Yilan County (TW); Yi-Ting Lai, Banciao (TW)

(73) Assignee: National Yunlin University of Science and Technology, Yunlin (TW)

( * ) Notice: Subject to any disclaimer, the term of this patent is extended or adjusted under 35 U.S.C. 154(b) by 376 days.

(21) Appl. No.: 11/024,669

(22) Filed: Dec. 30, 2004

(65) Prior Publication Data

US 2006/0029994 A1    Feb. 9, 2006

(30) Foreign Application Priority Data

Dec. 31, 2003   (TW) ............................... 92137624 A

(51) Int. Cl.
*C12Q 1/34*   (2006.01)
*C12N 11/14*  (2006.01)
*C12N 11/00*  (2006.01)

(52) U.S. Cl. .................... 435/18; 435/176; 204/403.14

(58) Field of Classification Search ............ None
See application file for complete search history.

(56) References Cited

U.S. PATENT DOCUMENTS

2004/0035699 A1* 2/2004 Hsiung et al. ............... 204/419

2004/0256685 A1* 12/2004 Chou et al. ................. 257/414

OTHER PUBLICATIONS

Dzyadevych et al. Biosensors Based on Enzyme Field-Effect Transistors for Determination of Some Substrates and Inhibitors; Analytical and Bioanalytical Chemistry, vol. 377 (2003) pp. 496-506.*
Brand et al. Penicillin G Biosensor Based on Penicillin Amidase Coupled to a Field Effect Transistor; Analytica Chimica Acta, vol. 226 (1989) pp. 87-97.*
Chi et al. Study on Extended Gate Field Effect Transistor With Tin Oxide Sensing Membrane; Materials Chemistry and Physics, vol. 63 (2000) pp. 19-23.*

* cited by examiner

*Primary Examiner*—Jon P Weber
*Assistant Examiner*—Paul C. Martin
(74) *Attorney, Agent, or Firm*—Muncy, Geissler, Olds & Lowe, PLLC

(57) ABSTRACT

A penicillin G biosensor, systems comprising the same, and measurement using the systems. The penicillin G biosensor has an extended gate field effect transistor (EGFET) structure and comprises a metal oxide semiconductor field effect transistor (MOSFET) on a semiconductor substrate, a sensing unit comprising a substrate, a tin oxide film on the substrate, and a penicillin G acylase film immobilized on the tin oxide film, and a conductive wire connecting the MOSFET and the sensing unit.

14 Claims, 4 Drawing Sheets

PENICILLIN G BIOSENSOR, SYSTEMS COMPRISING THE SAME, AND MEASUREMENT USING THE SYSTEMS

BACKGROUND

The invention relates to a biosensor, and more specifically to a biosensor measuring penicillin G concentration and systems comprising the same.

Penicillin is an antibiotic produced from penicillinum. Penicillin binding protein (PBP) is an essential enzyme used in synthesizing bacteria cell walls. When penicillin combines with PBP, synthesis of bacteria cell walls is inhibited. This is because PBP cannot supply enough proteins to synthesize bacteria cell walls after penicillin and PBP are combined, finally resulting in breakdown and death of cells.

Penicillin may cause serious allergies in 10~20% of the population, thus, it is advantageous to develop a method of detecting penicillin residue in food or cosmetics. Currently, penicillin residue can be detected using enzymes capable of decomposing penicillin, with the enzyme usually immobilized on a substrate. Enzyme immobilization can be accomplished using chemical and physical methods. A chemical method is disclosed in U.S. Pat. No. 6,060,268. A penicillin G acylase is immobilized on a cross-linked mixture by covalent bonds, wherein the cross-linked mixture comprises gelled gelling agents, such as gelatin, and a polymer containing free amino groups, such as alginate, amine, chitosan, or polyethylene imine.

Another chemical method is disclosed in U.S. Pat. No. 5,780,260. Penicillin G amidase, glutaryl-7-ACA acylase, or D-amino acid oxidase is immobilized on an amino-functional organosiloxane polymer carrier by covalent bonds. The covalent bonds are formed by activating amino groups on the carrier with a dialdehyde and reacting the activated groups with reactive groups on the enzyme.

A strong chemical bond may be formed between an enzyme and a monomer using the chemical methods. The chemical methods, however, have several drawbacks, for example, are expensive and complicated, and enzyme activity may easily be lost since an enzyme activity center usually participates in bonding. Physical methods are simple and conventionally used, but also have problems of enzyme loss due to no formation of covalent bonds.

A method of detecting penicillin concentration is disclosed in U.S. patent Ser. No. 10/028,079. A penicillinase is immobilized on a pH-sensitive hydrogel. When penicillic acid is produced by decomposing penicillin using the penicillinase, osmotic pressure of the hydrogel may alter as concentration of the penicillic acid alters. Penicillin concentration may thus be obtained by detecting variation of osmotic pressure using a pressure transducer. The method, however, may consume energy due to use of the pressure transducer, resulting in non-accurate measurement.

SUMMARY

The invention provides a penicillin G biosensor comprising an extended gate field effect transistor and a tin oxide sensitive film having a penicillin G acylase film immobilized thereon to detect penicillin G concentration in a solution. The invention provides low cost, high sensitivity of ion sensitive films, accurate measurement, and rapid response time.

The invention provides a system comprising an extended gate field effect transistor and measurement using the system to measure response curves of reaction time and recovery time of the extended gate field effect transistor.

The invention provides an extended gate field effect transistor structure comprising a metal oxide semiconductor field effect transistor (MOSFET), a sensing unit comprising a substrate and a tin oxide film thereon, and a conductive wire connecting the MOSFET and the sensing unit.

The invention provides a system of measuring pH value of a solution, comprising the above-mentioned extended gate field effect transistor, a reference electrode supplying stable voltage, a semiconductor characteristic instrument connecting the extended gate field effect transistor and the reference electrode, respectively, a temperature controller comprising a temperature control center, a thermocouple, a heater, and a light-isolation container isolating the sensing unit from photosensitive effect, wherein the temperature control center connects the thermocouple and the heater, respectively. Measurement of pH of a solution comprises pouring a solution into the light-isolation container, immersing the extended gate field effect transistor, the reference electrode, and the thermocouple in the solution, adjusting temperature of the solution by the heater controlled by the temperature control center after detecting temperature variation in the solution by the thermocouple, transmitting measurement data from the extended gate field effect transistor and the reference electrode to the semiconductor characteristic instrument, and reading out current-voltage (I-V) values of the solution by the semiconductor characteristic instrument to obtain pH value of the solution.

The invention provides a method of measuring sensitivity of a tin oxide extended gate field effect transistor, using the above-mentioned system, comprising immersing the tin oxide film of the tin oxide extended gate field effect transistor in an acidic or basic solution, recording a curve of source/drain current versus gate voltage of the tin oxide extended gate field effect transistor by the semiconductor characteristic instrument after altering pH values of the acidic or basic solution at a fixed temperature, and examining the curve to obtain a sensitivity of the tin oxide extended gate field effect transistor at the fixed temperature and a fixed current.

The invention also provides a system of measuring penicillin G concentration in a solution, comprising the above-mentioned penicillin G biosensor, a reference electrode supplying a stable voltage, an instrumentation amplifier having two inputs and one output, a high-resistance multimeter connecting the output of the instrumentation ampilfier, and a microcomputer pH meter, wherein the two inputs connect the penicillin G biosensor and the reference electrode, respectively. Measurement of penicillin G concentration in a solution comprises determining pH value of a solution by the microcomputer pH meter, immersing the penicillin G biosensor and the reference electrode in the solution, and reading out a response voltage of the sensing unit by the high-resistance multimeter to obtain penicillin G concentration in the solution.

The invention further provides a method of measuring a response of a penicillin G biosensor, using the above-mentioned system, comprising measuring pH value of a penicillin G solution by the microcomputer pH meter, immersing the penicillin G acylase film of the penicillin G biosensor in the penicillin G solution, recording an output voltage of the penicillin G biosensor by the high-resistance multimeter, and altering concentration of the penicillin G solution and repeating the first four steps to obtain a response of the penicillin G biosensor. The response is an output voltage variation between initial and terminal measuring points at a fixed pH value.

The sensing unit provided by the invention detects penicillin G with penicillin G acylase. Penicillin G acylase is hydrolase which transfers hydrogen atom, oxygen atom, or electrons of a substrate to another. The invention provides a biosensor comprising the enzyme and an extended gate field effect transistor.

Additionally, physical gel entrapment immobilizes a penicillin G acylase layer, which combines the semiconductor photolithography processes. Although enzyme may loss during long detection duration, disposable biosensors may effectively solve the problem at a low cost, and suitable for large-scale production.

A detailed description is given in the following embodiments with reference to the accompanying drawings.

BRIEF DESCRIPTION OF THE DRAWINGS

Embodiments of the invention can be more fully understood by reading the subsequent detailed description and examples with references made to the accompanying drawings, wherein.

DETAILED DESCRIPTION

Figure 1:
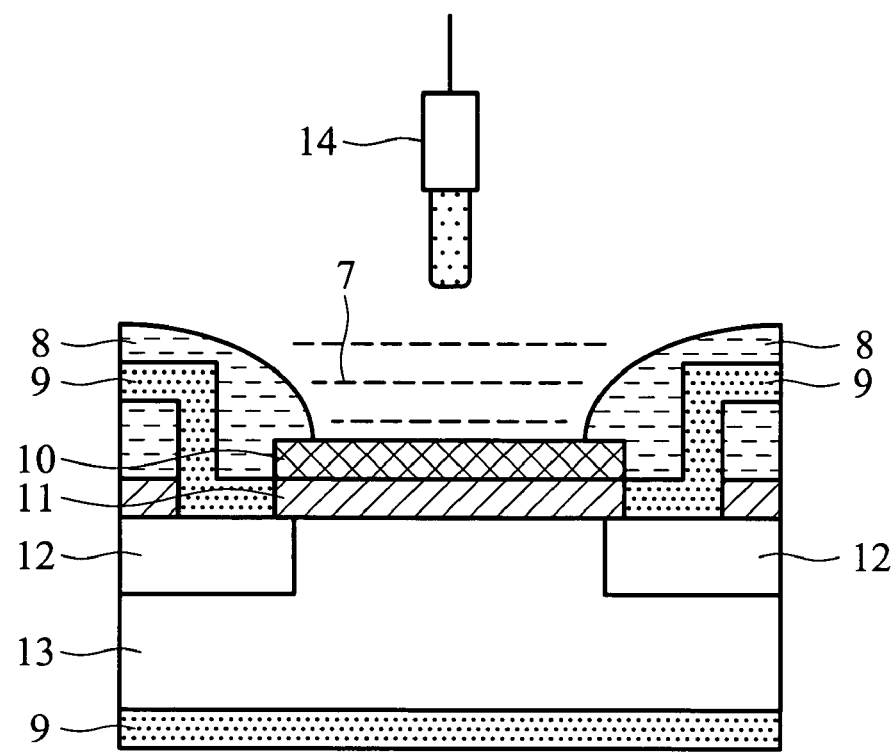
FIG. 1 is a cross-section of a conventional ion sensitive field effect transistor.

Referring to FIG. 1, a conventional ion sensitive field effect transistor (ISFET) comprises a p-type silicon substrate 13, a gate comprising a silicon dioxide film 11 on the substrate, and a sensitive film 10 immobilized on the film 11, wherein only the sensitive film 10 directly contacts a test solution 7. Other elements of the ISFET are covered by an insulation region 8 comprising epoxy resin. Both sides of the silicon dioxide film 11 in the substrate are n-type heavy doped regions (source/drain) 12. A conductive wire 9, such as aluminum wire, connects the transistor such that source/drain electronic signals can be transmitted to additional circuits thereby after the test solution 7 is detected by the sensitive film 10. Additionally, a reference electrode 14 supplying stable voltage avoids noise disturbance.

Figure 2:
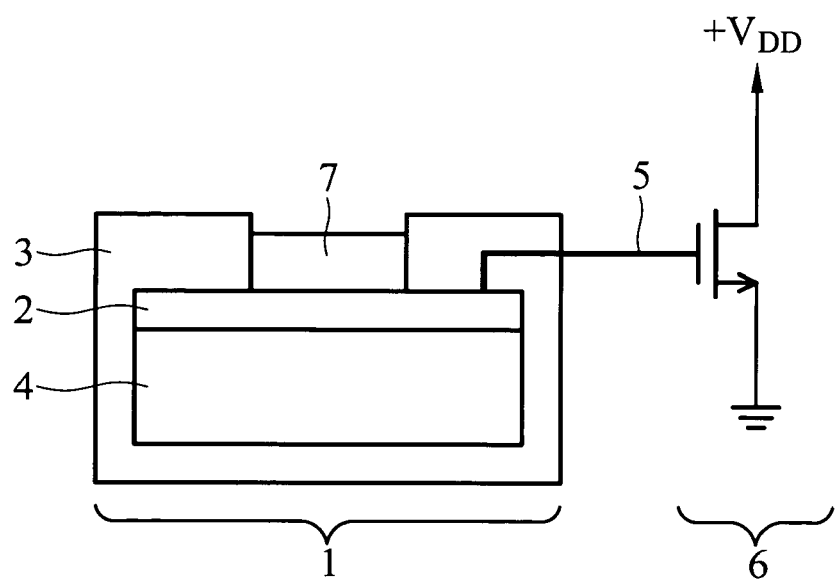
FIG. 2 is a cross-section of an extended gate field effect transistor of the invention.

An extended gate field effect transistor (EGFET) is developed from an ISFET. A sensitive film is isolated from a gate of an ISFET, that is, a metal oxide semiconductor field effect transistor (MOSFET) is completely isolated from a test solution to prevent unstable characteristics on semiconductor elements and decrease interference from the test solution. Referring to FIG. 2, an extended gate field effect transistor comprises a sensing unit 1 and a MOSFET 6, wherein the sensing unit 1 comprises a conductive glass 4, such as indium tin oxide (ITO) glass, and a tin oxide film 2 on the conductive glass 4. A conductive wire 5 connects the sensing unit 1 and the gate of the MOSFET 6. The sensing unit 1 is covered by an insulation region 3, exposing partial tin oxide film 2 to contact a test solution 7. Detection by an EGFET is described as follows. First, adsorbent hydrogen ions of a tin oxide sensitive film are converted to electronic signals. Threshold voltage of a MOSFET is then controlled by the electronic signals. Finally, hydrogen ion concentration is obtained by examining current values.

The invention provides a penicillin G biosensor which combines an enzyme reaction of penicillin G acylase and an EGFET having a tin oxide sensitive film thereon to detect penicillin G concentration in a solution. A penicillin G acylase layer is immobilized on a tin oxide sensitive film of an extended gate field effect transistor by gel entrapment. When penicillin G acylase contacts penicillin G residue, penicillin G residue may be hydrolyzed to hydrogen ions, resulting in pH value variation. The pH value variation is then converted to an electronic signal by the tin oxide film.

Figure 3:
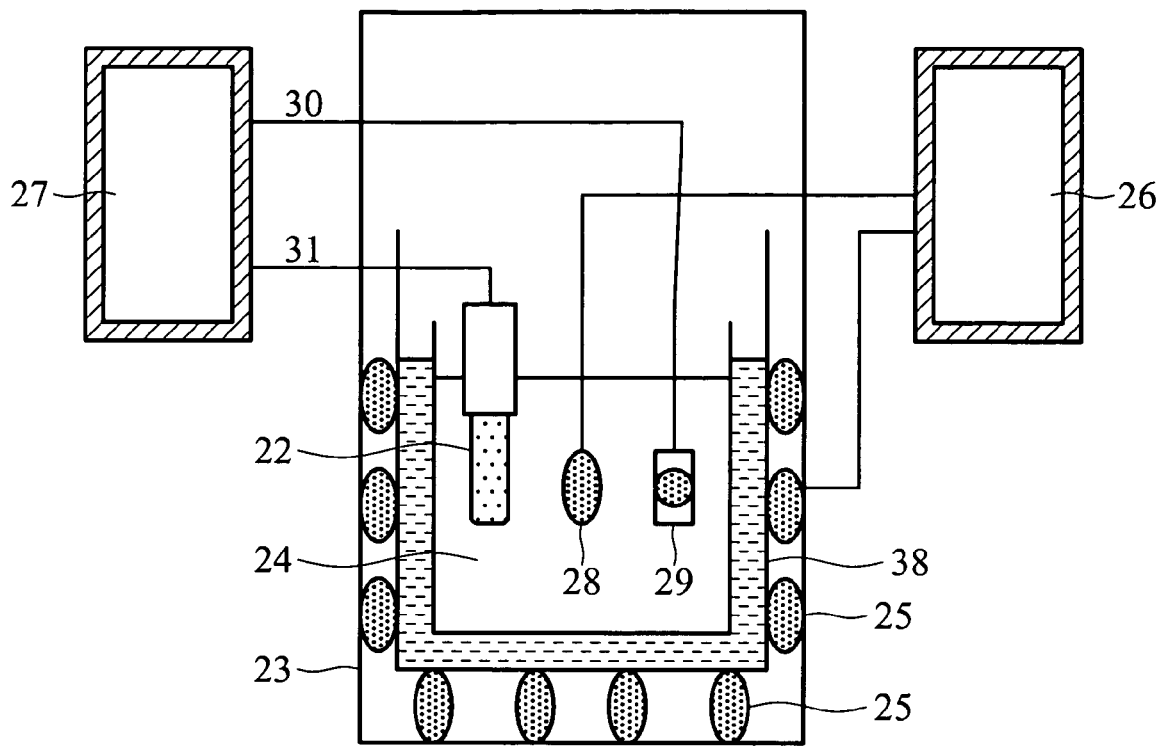
FIG. 3 shows a current-voltage system of measuring a sensitivity of a tin oxide film of the invention.

The current-voltage system showed in FIG. 3 measures sensitivity of a penicillin G biosensor. A sensing unit 29 of a tin oxide extended gate field effect transistor is immersed in a test solution 24 in a container 38. A semiconductor characteristic instrument 27, such as Keithley 236, connects a source and a drain of the sensing unit 29 by conductive wires 30, such as aluminum wire, to process electronic signals.

Additionally, a reference electrode 22 is immersed in the test solution 24 to supply stable voltage. The reference electrode 22 is an Ag/AgCl reference electrode. The reference electrode 22 connects the semiconductor characteristic instrument 27 by a conductive wire 31. A set of heaters 25 is installed outside the container, connecting a temperature controller 26 (temperature control center). When temperatures of the test solution 24 are altered, the temperature controller 26 may drive the heaters 25 to adjust the test solution temperature, wherein a thermocouple 28 of the temperature controller 26 detects the temperature of the test solution 24. The test solution 24, the heaters 25, and other elements contacting the test solution 24 are placed in a light-isolation container 23, such as a dark box, to prevent photosensitive effect.

The method of measuring sensitivity of a tin oxide extended gate field effect transistor using the above-mentioned system is described in the following. First, the tin oxide film of the tin oxide extended gate field effect transistor is immersed in a test solution. Subsequently, pH values of the test solution are altered from 2 to 8 at a fixed temperature, generally 25° C. Next, the semiconductor characteristic instrument supplies a voltage from 1 to 6V to the gate of the tin oxide extended gate field effect transistor, and a fixed voltage of 0.2V to the source/drain thereof. Next, a curve of source/drain current versus gate voltage of the tin oxide extended gate field effect transistor is recorded by the semiconductor characteristic instrument. Finally, the curve is examined to obtain a sensitivity of the tin oxide extended gate field effect transistor at the fixed temperature and a fixed current.

Figure 4:
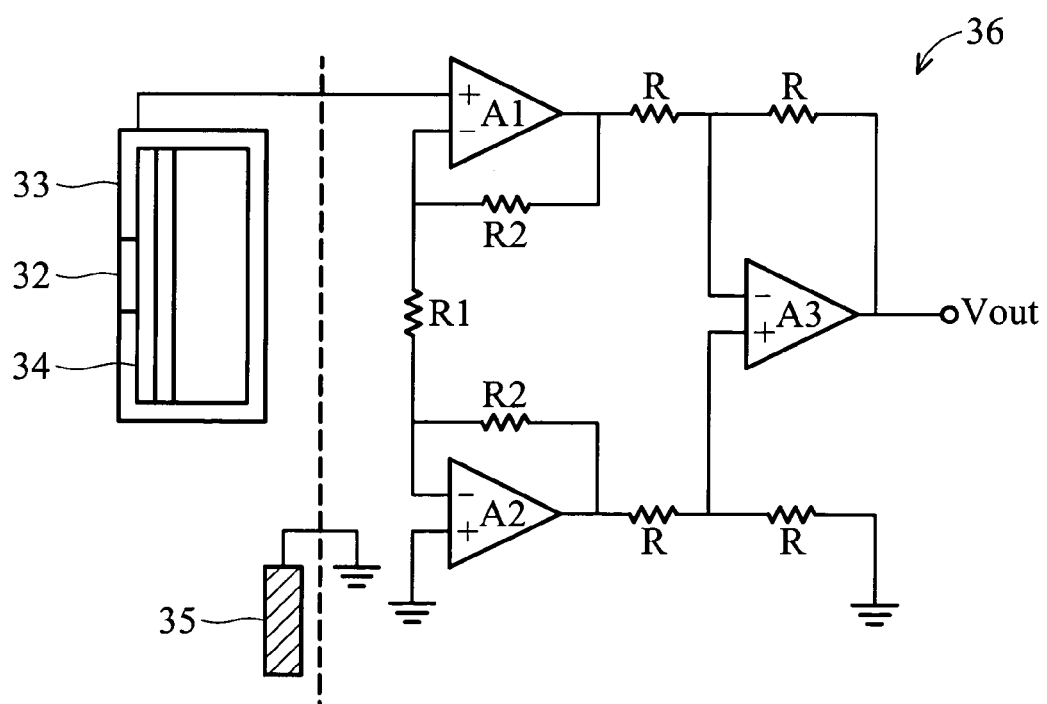
FIG. 4 shows a sensing unit and a readoutcircuit.

Additionally, electronic signals of the penicillin G biosensor 33 (comprising a penicillin G acylase film 32 and a tin oxide film 34) may be amplified, as shown in FIG. 4, and measured data of various test solutions can be read by an instrumentation ampilfier 36. A reference electrode 35 calibrates the measured data. The system comprises the above-mentioned penicillin G biosensor, a reference electrode, such as an Ag/AgCl reference electrode, supplying a stable voltage, an instrumentation amplifier, such as LT1167, having two inputs and one output, a high-resistance multimeter, such as HP34401A, and a microcomputer pH meter having pH range from 1 to 14 and a resolution of 0.01, wherein the penicillin G biosensor and the reference electrode connect the two inputs, respectively, and the high-resistance multimeter connects the output of the instrumentation ampilfier. Measurement of penicillin G concentration in a solution using the above-mentioned system is described in the following. First, pH value of a solution is determined by the microcomputer pH meter. Next, the penicillin G biosensor and the reference electrode are immersed in the solution. Finally, an output voltage of the sensing unit is readout by the high-resistance multimeter to obtain penicillin G concentration in the solution.

EXAMPLE

Manufacture of the Penicillin G Biosensor

Figure 5:
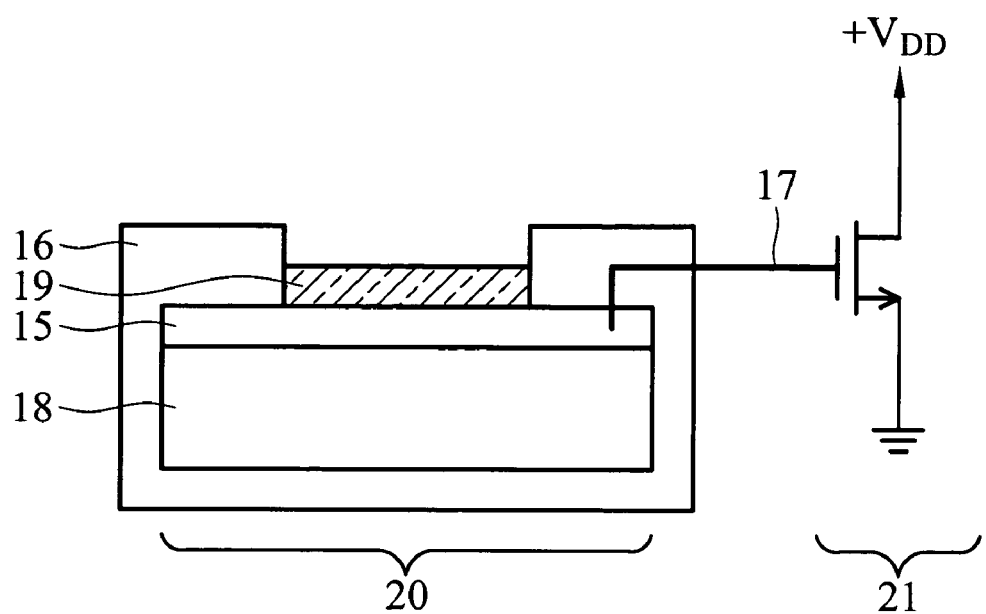
FIG. 5 is a cross-section of a biosensor having an immobilized penicillin G acylase of the invention.

Referring to FIG. 5, a cross-section of a penicillin G biosensor is illustrated. First, a 0.8 cm×0.5 cm tin oxide film 15 was prepared on an ITO glass 18 to form a sensing unit. The sensing unit was covered by epoxy resin 16, exposing partial tin oxide film 19 to form a sensing window of about 2 mm×2 mm. The sensing unit was connected with a gate of a MOSFET by an aluminum wire 17.

After the sensing unit and the transistor were packaged, a penicillin G acylase 14 was immobilized on the tin oxide film 15 by gel entrapment to form an enzyme sensor. The preparation of a penicillin G acylase mixing solution is described in the following. First, 80 mg PVA-SbQ (photopolymer, Toyo Gose, Kogyo Company, Japan) was added to 80 μl phosphate buffer solution (pH 7.5) to form 1M photopolymer solution. Next, the photopolymer solution (20 mM, pH 7.5) was mixed with penicillin G acylase solution (20 mM, pH 7.5, Sigma Chemical Company, USA) in ratios of 1:1, 2:1, and 3:1, preferably, 1:1 to form a penicillin G acylase mixing solution. 1 μl penicillin G acylase mixing solution was then dropped on the sensing window. After a drying period, the mixing solution was exposed under UV light (365 nm) for photopolymerization for 20 minutes. Next, the device was placed in a dark box at 4° C. for about 12 hours. The sensing window was cleaned in deionized water before measuring.

Preparation of the Penicillin G Test Solutions

A 20 mM phosphate buffer solution was first prepared by deionized water. The pH value of the buffer solution was adjusted to 7.5 by adding 20 mM potassium dihydrogen phosphate ($KH_2PO_4$, Sigma Chemical Company, USA) and 20 mM potassium dipotassium hydrogen phosphate ($K_2HPO_4$, Sigma Chemical Company, USA). Next, penicillin G test solutions with various concentrations were prepared. Proper amounts of penicillin G powders (Sigma Chemical Company, USA) were added to phosphate buffer solutions to form 1, 2, 5, and 10 mM penicillin G test solutions, respectively. As described above, pH values of the test solutions were adjusted to 7.5 by adding 20 mM potassium dihydrogen phosphate and 20 mM potassium dipotassium hydrogen phosphate.

The test solutions were placed in a dark box at 4° C. before measuring.

Measurement of the Test Solution Using the Current-voltage Measuring System

The current-voltage measuring system of the invention is illustrated in FIG. 3. A sensing unit 29 and an Ag/AgCl reference electrode 22 were immersed in a test solution 24. A current-voltage curve of an EGFET in the test solution was measured by a semiconductor characteristic instrument 27 (Keithley 236). The temperature of the test solution was controlled at 25° C.

The readout circuit of the penicillin G biosensor of the invention is illustrated in FIG. 4. A penicillin G biosensor 33 and an Ag/AgCl reference electrode 35 were immersed in a test solution. Biosensor response was obtained using a readout circuit 36.

Figure 6:
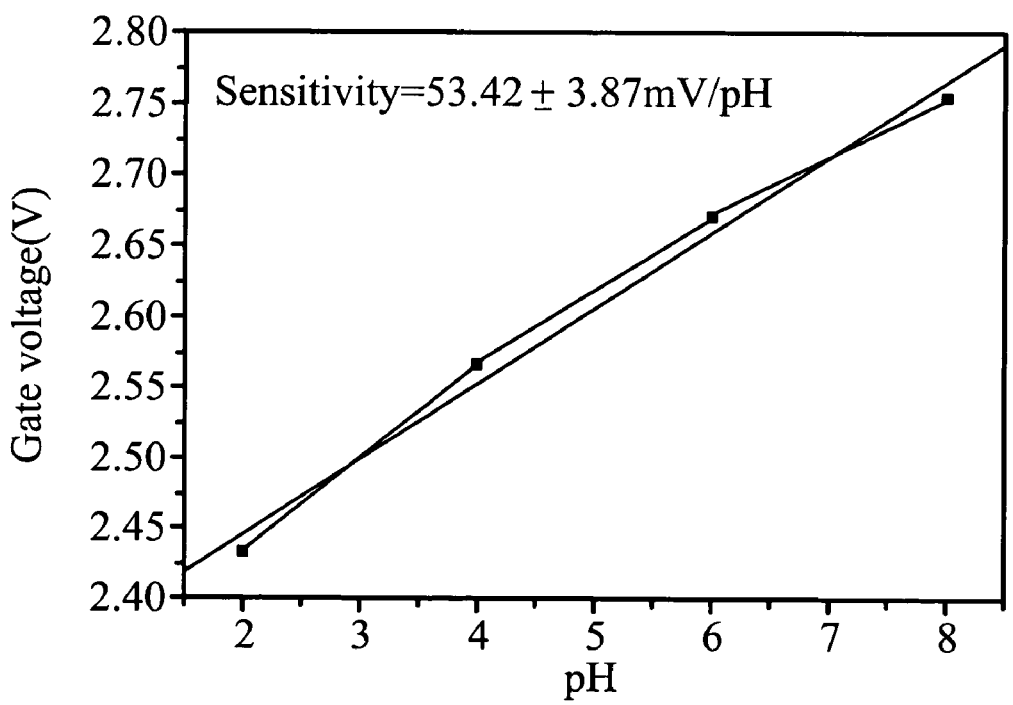
FIG. 6 shows the sensitivity of a tin oxide sensitive film in test solutions with various pH of the invention.

Measurement of a concentration of a penicillin G test solution is described in the following. First, a test solution was cooled to room temperature. Next, a penicillin G biosensor was immersed in a phosphate buffer solution for 20 sec, then in the test solution to measure voltage values. A voltage-time curve was then plotted by Microsoft Origin 6.0 according to the measuring data. Finally, the sensitivity of the tin oxide extended gate field effect transistor of the invention was obtained by analyzing the curve. The sensitivity was about 53.42 mV/pH, as shown in FIG. 6.

Figure 7:
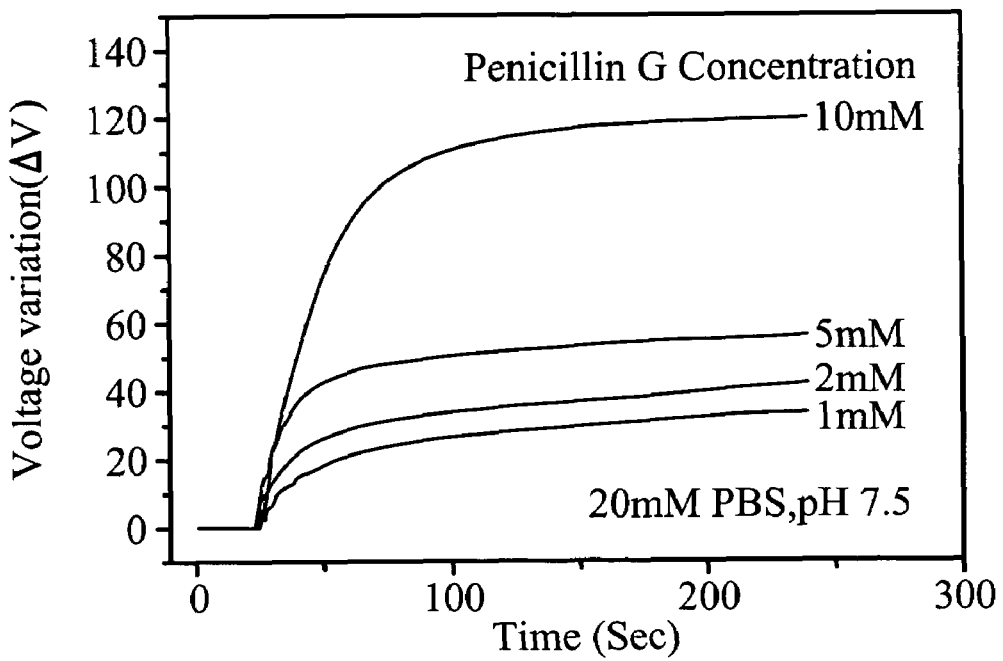
FIG. 7 shows voltage curves of test solutions with different concentrations in 20 mM phosphate buffer solution (PBS) (pH 7.5) of the invention.
Figure 8:
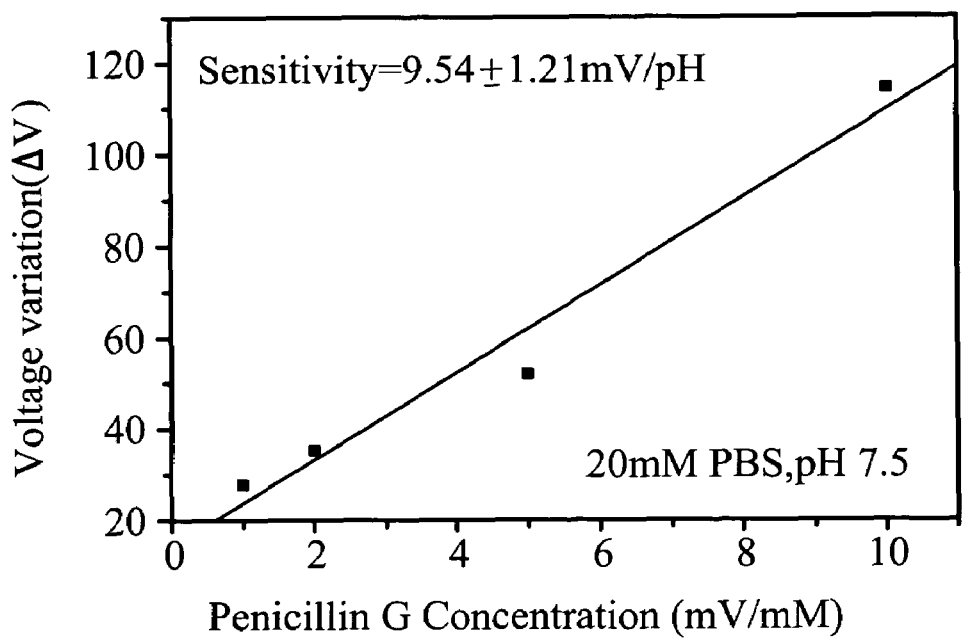
FIG. 8 shows an optimal linear sensitivity of the invention.

Additionally, 20 mM phosphate buffer solution with pH 7.5 was the best mode condition of the invention. FIG. 7 shows voltage curves of test solutions with various concentrations. The voltage variation may stabilize after a response time of about 100 sec, and the highest sensitivity of the penicillin G biosensor of the invention was about 9.54 mV/mM. FIG. 8 is a linear calibration of FIG. 7.

The above results indicate that, at pH 2 to 8, the sensitivity of the tin oxide extended gate field effect transistor of the invention was about 53.42±3.87 mV/pH. Optimal voltage curves of various test solutions are obtained using 20 mM phosphate buffer solution with pH 7.5. The linear sensitivity of the 1, 2, 5, and 10 mM test solutions was about 9.54±1.21 mV/mM. Thus, the invention has advantages of high sensitivity, accurate measurement, rapid response time, and low cost.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A penicillin G biosensor with an extended gate field effect transistor structure, comprising:
    a metal oxide semiconductor field effect transistor (MOSFET) on a semiconductor substrate;
    a sensing unit comprising a substrate, a tin oxide film on the substrate, and a penicillin G acylase film immobilized on the tin oxide film, wherein the penicillin G acylase film is formed by photopolymerization of a mixture of a photosensitive polymer phosphate buffer solution and a penicillin G acylase solution; and
    a conductive wire connecting the MOSFET and the sensing unit.

2. The penicillin G biosensor as claimed in claim 1, wherein the metal oxide semiconductor field effect transistor is an N-type field effect transistor.

3. The penicillin G biosensor as claimed in claim 1, wherein the conductive wire connects a gate of the metal oxide semiconductor field effect transistor and the sensing unit.

4. The penicillin G biosensor as claimed in claim 1, wherein the substrate is a conductive glass.

5. The penicillin G biosensor as claimed in claim 4, wherein the substrate is an indium tin oxide glass.

6. The penicillin G biosensor as claimed in claim 1, wherein the penicillin G acylase film is immobilized on the tin oxide film by gel entrapment.

7. The penicillin G biosensor as claimed in claim 1, wherein the photosensitive polymer phosphate buffer solution and the penicillin G acylase solution are in a ratio of 1:1.

8. The penicillin G biosensor as claimed in claim 1, further comprising an insulating layer on the surface of the sensing unit.

9. The penicillin G biosensor as claimed in claim 8, wherein the insulating layer comprises epoxy resin.

10. A system of measuring a concentration of penicillin G in a solution, comprising:
- a penicillin G biosensor as claimed in claim 1;
- a reference electrode supplying a stable voltage;
- an instrumentation amplifier having two inputs and one output, wherein the two inputs connect the penicillin G biosensor and the reference electrode, respectively;
- a high-resistance multimeter connecting the output of the instrumentation amplifier; and
- a microcomputer pH meter, wherein Measurement of a concentration of penicillin G in a solution comprises determining pH value of a solution by the microcomputer pH meter, immersing the penicillin G biosensor and the reference electrode in the solution, and reading out a response voltage of the sensing unit by the high-resistance multimeter.

11. The system as claimed in claim 10, wherein the high-resistance multimeter is HP34401A.

12. The system as claimed in claim 10, wherein the instrumentation amplifier is LT1167.

13. The system as claimed in claim 10, wherein the microcomputer pH meter has pH range from 1 to 14, and a resolution of 0.01.

14. The system as claimed in claim 10, wherein the reference electrode is an Ag/AgCl reference electrode.

* * * * *